US010662835B2

United States Patent
Andersen et al.

(10) Patent No.: US 10,662,835 B2
(45) Date of Patent: May 26, 2020

(54) APPARATUS FOR IDENTIFYING FLUID OF A REMOVABLE FLUID CONTAINER AND METHOD OF USE

(71) Applicant: Castrol Limited, Pangbourne, Reading (GB)

(72) Inventors: Jens Andersen, Berkshire (GB); Steven Paul Goodier, Berkshire (GB); Hanna Hellman, Berkshire (GB); Andrea Leeson, Kent (GB)

(73) Assignee: Castrol Limited, Reading (GB)

( * ) Notice: Subject to any disclaimer, the term of this patent is extended or adjusted under 35 U.S.C. 154(b) by 0 days.

(21) Appl. No.: 16/194,318

(22) Filed: Nov. 17, 2018

(65) Prior Publication Data
US 2019/0085741 A1 Mar. 21, 2019

Related U.S. Application Data

(63) Continuation of application No. 15/312,584, filed as application No. PCT/EP2015/061337 on May 21, 2015, now Pat. No. 10,167,755.

(30) Foreign Application Priority Data

May 21, 2014 (GB) .................................. 1409086.4

(51) Int. Cl.
*G01N 33/28* (2006.01)
*F01M 11/04* (2006.01)
(Continued)

(52) U.S. Cl.
CPC ..... *F01M 11/0458* (2013.01); *F01M 11/0004* (2013.01); *F01M 11/04* (2013.01); *F01M 11/10* (2013.01); *F16N 37/00* (2013.01); *G01G 19/08* (2013.01); *G01N 33/2888* (2013.01); *F01M 2011/0095* (2013.01); *F01M 2011/0483* (2013.01); *F16N 19/00* (2013.01);
(Continued)

(58) Field of Classification Search
CPC .................................................. G01N 33/2888
See application file for complete search history.

(56) References Cited

U.S. PATENT DOCUMENTS 4,151,823 A 5/1979 Grosse et al.
5,085,188 A * 2/1992 Gasparri .................. F01M 1/10
123/196 A
(Continued)

FOREIGN PATENT DOCUMENTS

CN 1836095 9/2006
DE 102012024365 6/2014
(Continued)

*Primary Examiner* — Todd M Melton
(74) *Attorney, Agent, or Firm* — McDonnell Boehnen Hulbert & Berghoff LLP

(57) ABSTRACT

An apparatus comprising: an identity determiner configured to determine an identity of a removable fluid container; a characteristic determiner configured to obtain a first characteristic based on testing the fluid of the fluid container; a data obtainer configured to obtain a second characteristic based on the identity; and a processor configured to control a fluid provider to provide fluid from the removable fluid container based on the comparison of the first characteristic and the second characteristic.

20 Claims, 3 Drawing Sheets

Figure 1A:
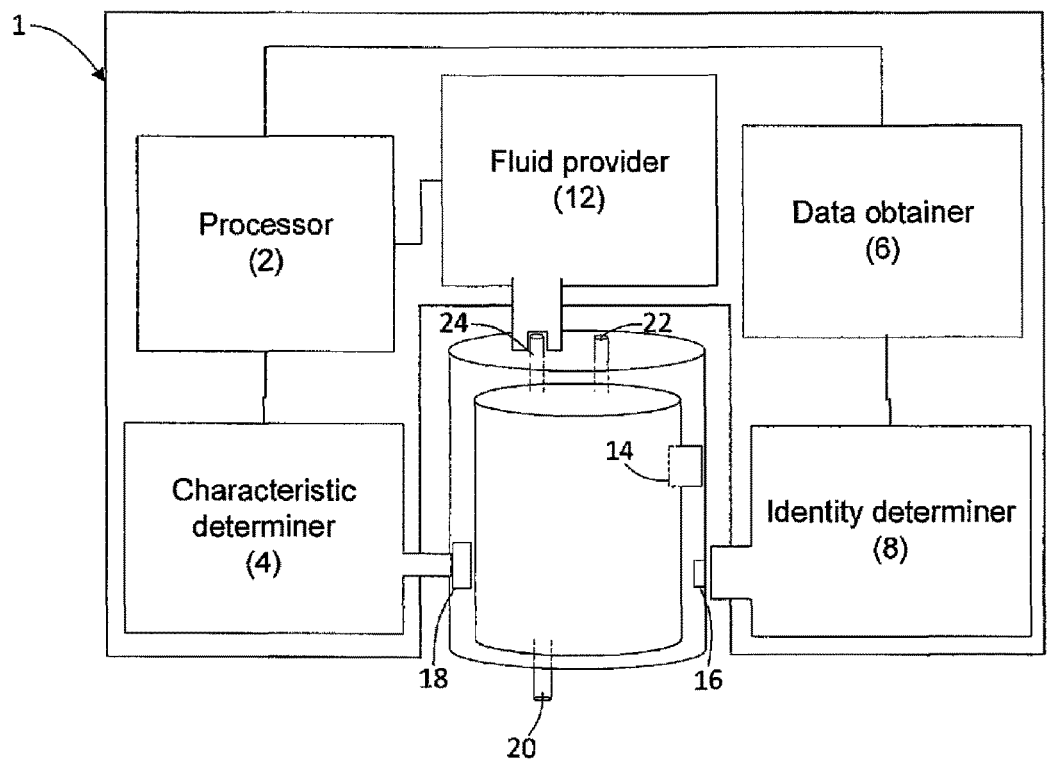

(51) Int. Cl.
  *G01G 19/08* (2006.01)
  *F01M 11/10* (2006.01)
  *F16N 37/00* (2006.01)
  *F01M 11/00* (2006.01)
  *F16N 19/00* (2006.01)

(52) U.S. Cl.
  CPC ...... *F16N 2200/12* (2013.01); *F16N 2250/18* (2013.01); *F16N 2250/34* (2013.01); *F16N 2250/36* (2013.01); *F16N 2250/50* (2013.01)

(56) References Cited

U.S. PATENT DOCUMENTS

| | | | |
|---|---|---|---|
| 5,454,354 | A | 10/1995 | Miller |
| 2002/0178780 | A1 | 12/2002 | Van Mullekom et al. |
| 2005/0066711 | A1 | 3/2005 | Discenzo |
| 2009/0254240 | A1 | 10/2009 | Olsen et al. |
| 2010/0312601 | A1* | 12/2010 | Lin .................. G06Q 10/0637 705/7.36 |
| 2011/0131269 | A1 | 6/2011 | Gilleland et al. |
| 2011/0253092 | A1 | 10/2011 | Springer et al. |
| 2013/0197738 | A1 | 8/2013 | Dvorak et al. |
| 2015/0291317 | A1 | 10/2015 | Brett et al. |
| 2015/0291318 | A1 | 10/2015 | Barnes et al. |
| 2015/0292371 | A1 | 10/2015 | Barnes et al. |
| 2015/0292372 | A1 | 10/2015 | Barnes et al. |
| 2015/0292674 | A1 | 10/2015 | Brett et al. |
| 2017/0089234 | A1 | 3/2017 | Dawson et al. |
| 2017/0089235 | A1 | 3/2017 | Dawson et al. |
| 2017/0089236 | A1 | 3/2017 | Andersen |
| 2017/0101911 | A1 | 4/2017 | Barnes et al. |
| 2017/0107873 | A1 | 4/2017 | Ali et al. |
| 2017/0122151 | A1 | 5/2017 | Brett et al. |
| 2017/0183992 | A1 | 6/2017 | Barnes et al. |
| 2017/0190466 | A1 | 7/2017 | Andersen et al. |
| 2017/0197596 | A1 | 7/2017 | Barnes et al. |

FOREIGN PATENT DOCUMENTS

| | | |
|---|---|---|
| EP | 2 259 216 | 12/2010 |
| JP | H04 142300 | 5/1992 |
| JP | 2003-149149 | 5/2003 |
| JP | 2007-297113 | 11/2007 |
| JP | 2008-180198 | 8/2008 |
| JP | 2011-028715 | 2/2011 |
| WO | WO 1999/65695 | 12/1999 |
| WO | WO 2003/070351 | 8/2003 |
| WO | WO 2014/076319 | 5/2014 |
| WO | WO 2016/158971 | 10/2016 |

* cited by examiner

APPARATUS FOR IDENTIFYING FLUID OF A REMOVABLE FLUID CONTAINER AND METHOD OF USE

CROSS REFERENCE TO RELATED APPLICATIONS

The present application is a continuation of U.S. patent application Ser. No. 15/312,584, filed on Nov. 18, 2016, which is a National Phase application of, and claims the benefit of, International (PCT) Application No. PCT/EP2015/061337, filed on May 21, 2015, which claims priority to GB Application No. 1409086.4, filed on May 21, 2014, the entire contents of each of which are incorporated herein by reference.

The present disclosure relates to apparatus and methods for the recycling of fluids, and for controlling the extraction of fluids from fluid containers to enable those fluids to be recycled, for example this control may be based on an assessment of the fluid in a removable fluid container.

Many vehicle engines use one or more fluids for their operation. Such fluids are often liquids. For example, internal combustion engines use liquid lubricating oil. Also, electric engines use heat exchange liquids for example to cool the engine, to heat the engine or to cool and heat the engine during different operating conditions. Such fluids are generally held in reservoirs associated with the engine and may require periodic replacement.

Replacement of engine lubricating oil in a vehicle engine usually involves draining the lubricating oil composition from the engine sump. The process may also involve removing and replacing the engine oil filter. Such a procedure usually requires access to the engine sump drain plug and oil filter from the underside of the engine, may require the use of hand tools and usually requires a suitable collection method for the drained lubricating oil composition.

Closed circulation fluid systems also exist. In particular hydraulic systems, and heat exchangers such as refrigeration apparatus and heat pumps provide examples of fluid circulation systems in which the performance qualities of the fluid may degrade over time.

Aspects and embodiments of the present disclosure may be directed to the recycling of fluids from such closed circulation systems and are set out in the appended claims.

Figure 1B:
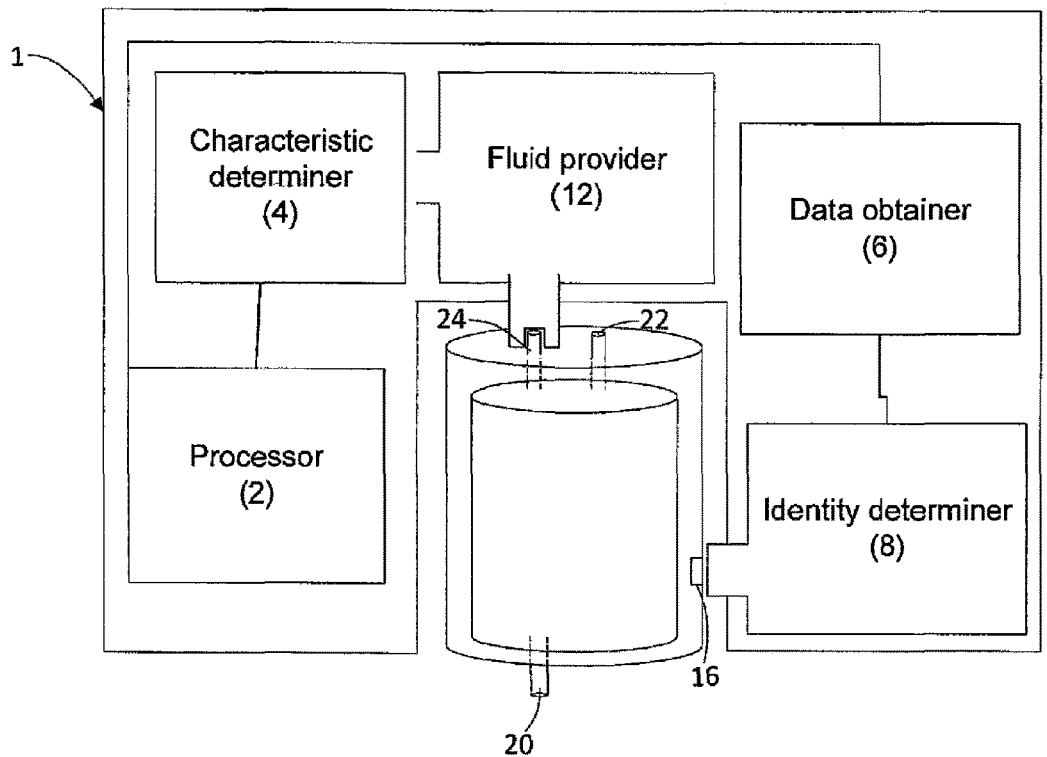
Figure 2C:
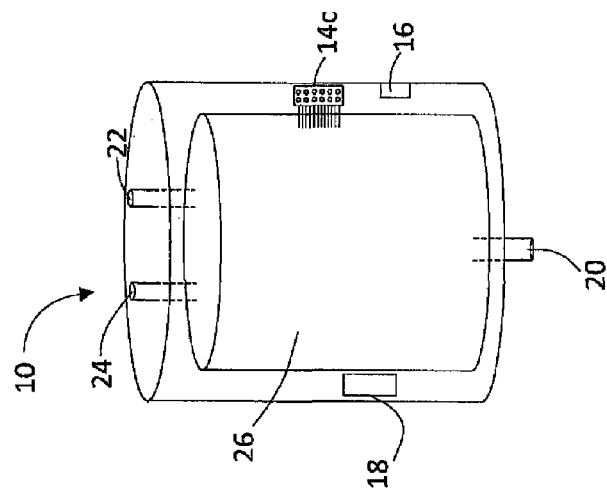
Figure 2B:
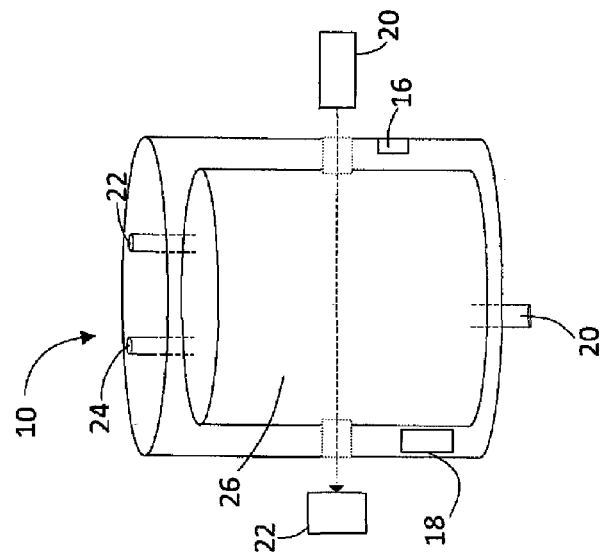
Figure 2A:
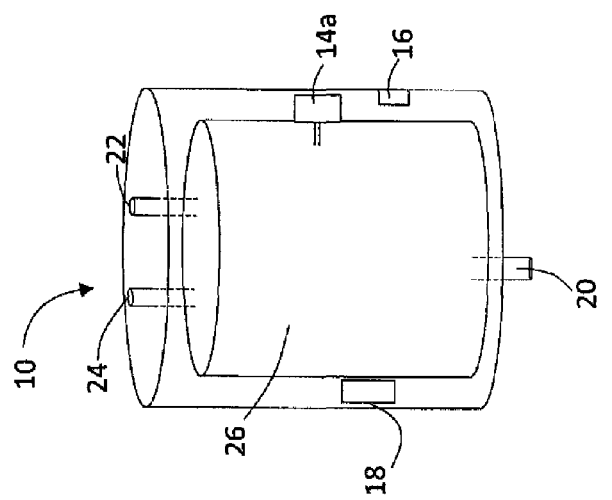
Figure 3:
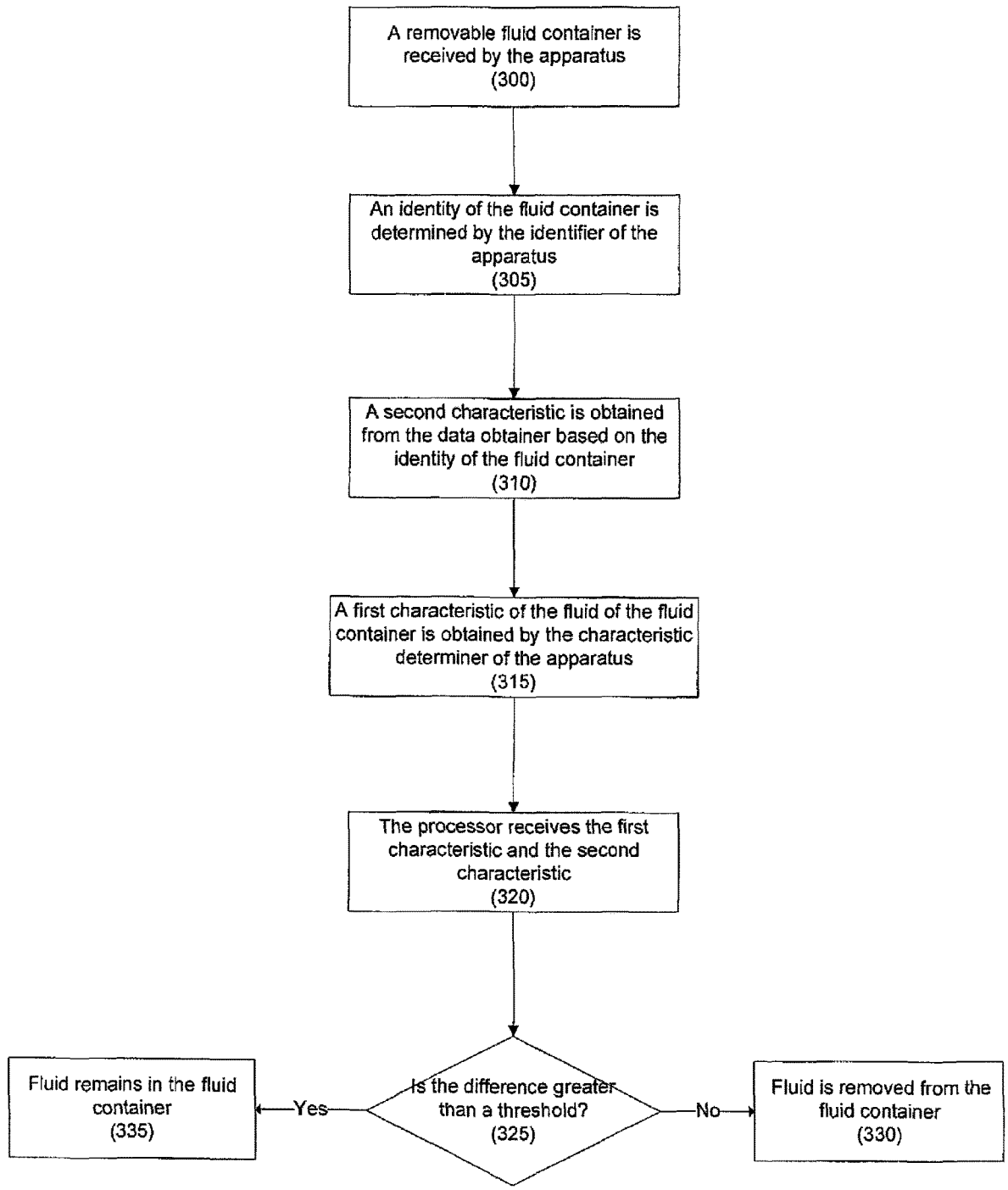

Some embodiments will now be described, by way of example only, with reference to the accompanying drawings, in which:

FIG. 1a illustrates an apparatus;
FIG. 1b illustrates another apparatus;
FIG. 2a shows a schematic diagram of a removable fluid container suitable for use with the apparatus of FIG. 1;
FIG. 2b shows a schematic diagram of another removable fluid container suitable for use with the apparatus of FIG. 1;
FIG. 2c shows a schematic diagram of another removable fluid container suitable for use with the apparatus of FIG. 1; and
FIG. 3 shows a flow diagram illustrating a method of the disclosure.

In the drawings like reference numerals are used to indicate like elements.

Synthetic oils are expensive to manufacture, and mineral oils may be derived from nonrenewable resources. Aspects of the disclosure are directed to the recycling of these and other fluids.

Aspects of the disclosure relate to selecting the best of a variety of different recycling methods for recycling a fluid. Embodiments of the disclosure also relate to avoiding mixing of different types of fluids thereby enabling them to be recycled without the need to separate mixtures. Closed fluid circulation systems may use removable replaceable fluid containers. Aspects of the disclosure aim to identify these containers, and to verify their contents to enable their contents to be recycled using a process appropriate for the particular type of fluid they contain.

The disclosure relates to a method for verifying a fluid to be recycled. This method may comprise obtaining an identifier from a container and using that identifier to obtain information describing fluid which should be carried by that container. For example, the identifier can be used to retrieve data from memory describing a characteristic of the fluid that that container is believed to carry. The method may comprise testing fluid carried by the container, and checking the results of that test against the information obtained using the identifier.

FIG. 1a shows an apparatus 1 comprising a processor 2, a data obtainer 6, a characteristic determiner 4, an identity determiner 8, and a fluid provider 12.

The processor 2 is coupled to the data obtainer, the fluid provider 12 and the characteristic determiner. The data obtainer 6 is coupled to the identity determiner.

As illustrated in FIG. 1a, the apparatus 1 may be coupled to a removable fluid container 10 for verifying the container and/or the fluid it contains before fluid is extracted from the container.

The characteristic determiner is configured to obtain data describing a first characteristic, such as a characteristic of the fluid carried by the container, and to provide that first characteristic to the processor. The characteristic determiner may be configured to determine this characteristic by testing the fluid carried by the container, or it may comprise an interface for obtaining data from a transducer carried by the container. This is described in more detail below with reference to FIG. 2a, FIG. 2b, and FIG. 2c.

The identity determiner 8 is arranged for obtaining an identifier from a fluid container, and for providing that identifier to the data obtainer. The data obtainer 6 is configured to use the identifier to obtain data describing a second characteristic of the container, and to provide this data to the processor 2. For example the data obtainer 6 may be configured to use the identifier to retrieve data from a data store, such as a memory, for example by using the identifier as an index into a look-up-table (LUT). This memory may be carried by the apparatus or the data obtainer 6 may be configured to communicate over a network to retrieve the data from a remote data store such as a server.

The fluid provider 12 is arranged to be controlled by the processor 2 and is operable to drain fluid from a fluid container, and to provide that fluid to the apparatus, or another apparatus. For example the fluid provider 12 may be controllable by the processor 2 to drain the fluid by extracting it for example by displacing it from the container, or by drawing it out.

The processor 2 is configured to obtain the first characteristic data from the characteristic determiner, and the second characteristic data from the data obtainer 6. The processor 2 is further configured to compare the first characteristic to the second characteristic, and to control the fluid provider 12 based on this comparison.

As illustrated in FIG. 1a, a removable fluid container 10 may comprise a fluid inlet 22, a fluid outlet 24 and optionally a vent 20 arranged to allow fluid to be introduced to or removed from the fluid container. The fluid container may comprise an identifier, and a sensor configured to sense a characteristic of a fluid carried by the container. The fluid container may also comprise a data store 18, such as a memory. Examples of containers that may be used with examples of the present disclosure are described in International patent application PCT/EP2013/074209, the entirety of which is hereby incorporated by reference.

In operation, a fluid container containing fluid to be recycled may be removed from a vehicle in which it has been used to supply fluid to a fluid circulation system of the vehicle. The container can then be presented to the apparatus and arranged so that the identity determiner 8 can read the identifier carried by the container and the characteristic determiner can obtain first characteristic data from the container. For example, the characteristic determiner may provide test data obtained from testing the fluid carried by the container, for example this test data may comprise at least one of the opacity, conductivity, viscosity, dielectric constant, and acidity of the fluid.

The identity determiner 8 provides the identifier to the data obtainer 6 which then provides the second characteristic data to the processor. For example, the second characteristic may comprise the type of fluid that the identifier indicates is carried by the container, for example it may be related to the usage history of the container and may for example describe the vehicle in which the fluid container has been used.

The characteristic determiner provides the first characteristic data to the processor 2 and the processor 2 performs a comparison based on the first characteristic and the second characteristic. For example, the first characteristic data may be an age dependent characteristic of the fluid, such as its viscosity or opacity. As mentioned above, the second characteristic may be related to usage history, for example it may comprise the age of the fluid thought to be stored in the container.

Accordingly, the processor 2 may be configured to use the second characteristic (such as the age of the fluid) to determine an expected value, or an expected range of values of the first characteristic (e.g. an age related characteristic). The processor 2 can then compare the actual value of the first characteristic to this expected value or range of values to verify that the fluid meets these expectations. The processor 2 can then control the fluid provider 12 to control the draining of fluid from the container based on this comparison. For example, if the first, tested (for example measured), characteristic of the fluid does not match that which is expected based on the identifier, the fluid may be contaminated or counterfeit, and so can be rejected from the recycling process.

The identity determiner 8 may be configured to read a machine readable marker carried by the container. For example the identity determiner 8 may comprise a wireless communication interface, examples of such wireless communication interfaces comprise optical, capacitive and/or inductive communicators. Examples of such interfaces include near field communicator such as a capacitive or inductive coupling interface such as might be provided by near field RF communicators for example NFC and RFID communicators. Where the identity determiner 8 comprises an optical interface it may be configured to identify the container based on an optical identifier such as a serial number, barcode, a QR code, or one or more colour coded markers. In some embodiments, the identity determiner 8 may be configured to identify the container based on one or more geometric features of the container such as a geometric keying, surface feature, cross section or shape.

The identity determiner 8 may comprise a wired communication interface arranged to couple with contacts carried by the container for electronic or optical communication.

For example, the container may carry a data provider such as a data store comprising electronic memory, and the identity determiner 8 may be configured to read this memory to obtain an identifier of the container.

Regardless of how the identity of the container is determined, the data obtainer 6 may use the identity to obtain second characteristic data comprising a value or range of values associated with at least one property of the fluid selected from the group consisting of: the amount of fluid, the temperature of fluid, the pressure of fluid, the viscosity of fluid, the viscosity index of the fluid, the density of fluid, the electrical resistance of fluid, the dielectric constant of fluid, the opacity of fluid, the chemical composition of fluid, the origin of the fluid and combinations of two or more thereof.

The fluid container may have previously been removably seated by means of a dock in a vehicle to supply, during operation of the vehicle, fluid to a fluid circulation system of vehicle, for example a fluid circulation system associated with the vehicle engine. As another possibility, the fluid container may have previously been removably seated by means of a dock to supply fluid, during operation, to a fluid circulation system associated with an engine other than a vehicle engine or to a reverse engine or generator or a turbine such as a wind turbine. The fluid container will have contained fluid before being removably seated.

As stated above the second characteristic may be determined based on the identity of the fluid container, this will now be described in more detail with reference to FIG. 1*a*.

FIG. 1*a* shows the apparatus coupled to the removable fluid container. The apparatus 1 is configured to receive the identity of the fluid container. The fluid container has a pre-defined identity and the identity determiner 8 of the apparatus 1 can determine the pre-defined identity from the identifier 16 of the fluid container 10. In the example shown in FIG. 1*a* the identifier 16 of the fluid container 10 may be a barcode and the identity determiner 8 of the apparatus 1 determines the identity of the fluid container by scanning the barcode.

One or more characteristics of the fluid in the fluid container are stored along with the identity of the container. The apparatus can therefore determine one or more characteristics based on the determined identity of the fluid container. In the example illustrated in FIG. 1*a* the apparatus comprises a data store (not shown) with a look-up table, and the look-up table comprises the identity of the fluid container and one or more characteristics of the fluid in the fluid container.

The second characteristic may be an inherent property of the fluid in the fluid container, for example the chemical composition, a class of fluid, and/or viscosity of the fluid. The second characteristic may also be a characteristic of the fluid based on the usage history of the fluid, for example an operation of the fluid during use. In an example where the fluid container is installed in an engine operational history of the engine may be stored and the second characteristic may be based on the operational history of the engine.

In the example shown in FIG. 1*a* the apparatus 1 obtains the one or more characteristics of the fluid in the fluid container 10 based on the measurement of the fluid from the sensor 14 of the fluid container 10. The fluid container 10 stores the one or more characteristics determined from the measurement of the fluid by the sensor 14 in the data store. The characteristic determiner 4 of the apparatus 1 may be configured to be coupled to a data store 18 such as a memory carried by the fluid container 10, such that data corresponding to the one or more measured characteristics can be obtained from this data store by the apparatus via the coupling.

As stated above the characteristic determiner may be configured to determine the first characteristic by testing the fluid carried by the container, or it may comprise an interface for obtaining data from a transducer carried by the container and this will now be described in more detail with reference to FIG. 2a, FIG. 2b and FIG. 2c. As illustrated in FIG. 2a, FIG. 2b, and FIG. 2c, the fluid of the fluid container 10 may be tested using an in-situ measurement (without removing fluid from the fluid container) with the fluid container 10 and/or apparatus 1 comprising a sensor to allow measurement of the fluid in the fluid container.

The characteristic may be measured with a sensor located on the fluid container, the examples shown in FIG. 2a and FIG. 2c show a sensor coupled to the fluid reservoir of the fluid container. The sensor may store data in a memory of the fluid container based on the output of the sensor 14. An in-situ measurement may also be made by a sensor coupled to the apparatus, as shown in FIG. 2b.

Embodiments of the apparatus shown in FIG. 1a may comprise an interface, such as conductive contacts, configured to couple with a sensor such as the capacitor, for example the characteristic determiner may comprise an electrical coupling configured to apply a test signal to a sensor such as the capacitor illustrated in FIG. 2a. In some examples the sensor carried by the container may be active in the sense that no test signal needs to be applied, for example the sensor may be coupled to a power supply carried by the container, or it may be configured to derive power from some other source. The interface of the characteristic determiner may comprise an inductive or capacitive coupling. For example the characteristic determiner may comprise an inductive coupler configured to provide a time varying H-field for coupling with a similar inductive coupler carried by the container. This inductive coupler may be configured to derive power from the H-field and to provide this power to a sensor carried by the container for providing the first characteristic to the characteristic determiner. As another example the interface may comprise a capacitive coupling. For example the sensor may comprise a single capacitive plate disposed in the fluid of the container, for example near a wall of the container, and the characteristic determiner may comprise a complementary capacitive plate configured to couple capacitively with the plate in the container through a wall of the container.

FIG. 2a shows a fluid container 10 with a capacitive sensor 14a. The capacitive sensor illustrated in FIG. 2a comprises two plates coupled to the fluid of the fluid reservoir 12. One or more characteristics of the fluid in the fluid reservoir can be determined from the change in electrical properties of this capacitor. For example, the electrical conductivity of the fluid may be dependent on the condition of the fluid, with the change in conductivity of the fluid altering output of the capacitor, for example the response of the capacitor to a test signal such as a test voltage and/or current.

FIG. 2b shows an example of a remote measurement of a characteristic of the fluid such as may be performed by the characteristic determiner of the apparatus of FIG. 1. In the example shown the fluid is measured using an optical measurement. The container comprises at least one optically transmissive portion, such as a window, for example a first window 21 and a second window 23 that allow the transmission of electromagnetic radiation from an electromagnetic radiation source 20 into the fluid of the container to be collected by a detector 22.

In this example the characteristic determiner comprises a source of optical electromagnetic radiation, such as a microwave, infrared, optical, ultraviolet or X-ray source, for example a laser or LED. This radiation source may be arranged to be directed through a transmissive portion of the container, such as a window and through some of the fluid. The characteristic determiner may comprise a detector arranged to determine a change in optical properties of the radiation caused by transmission through the fluid. The characteristic determiner may be configured to use this to determine a characteristic of the fluid. The electromagnetic radiation source may emits electromagnetic radiation in the infrared spectrum and the detector may comprise an infrared spectrometer. The absorption of characteristic wavelengths of the spectrum may be used to determine the composition of the fluid and accordingly this may allow one or more characteristics of the fluid to be determined.

The example shown in FIG. 2c comprises a fluid reservoir with a multichannel sensor 14c. The electrical properties of the fluid in the fluid container may be measured using a multichannel probe. The change in electrical response between one or more of the probes coupled to the fluid will allow one or more electronic characteristics of the fluid to determined. It will be appreciated therefore that the characteristic determiner may be configured to obtain a combination of measurements of the fluid based on any one or more of the techniques described above with reference to FIG. 2a and FIG. 2b.

FIG. 1b illustrates another apparatus similar to that described above with reference to FIG. 1a. The apparatus of FIG. 1b comprises all of the features described above with reference to FIG. 1a with the exception of the characteristic determiner. The characteristic determiner illustrated in FIG. 1b is coupled to the fluid provider 12 for making ex situ measurements of the fluid (e.g. outside the container).

In the example illustrated in FIG. 1b, the fluid provider 12 is configured to obtain a sample of fluid from a fluid container, and to provide that fluid to the characteristic determiner.

As illustrated in FIG. 1b, a characteristic of the fluid may be determined from an ex-situ measurement. An ex-situ measurement may be made by removing at least part of the fluid from the fluid container and measuring one or more characteristics of the fluid extracted. The fluid provider 12 may be coupled to obtain the sample from the fluid inlet 22, fluid outlet 24 and/or vent 20 of the fluid container 10. In the example shown in FIG. 1b the characteristic determiner 4 is coupled to the fluid provider 12, such that the characteristic determiner 4 receives fluid from the fluid provider 12 which in turn receives fluid from the fluid container via the fluid outlet 24.

The first characteristic, based on testing the fluid, corresponds to a characteristic of the fluid in the fluid container. The second characteristic, based on the identity of the fluid container, corresponds to a stored characteristic of the fluid in the fluid container. The first characteristic therefore represents one or more characteristics of the fluid at the time of testing and the second characteristic represents an expected characteristic of the fluid in the fluid container.

The characteristic determiner 4 is configured to determine a first characteristic of the fluid by testing at least a portion of the fluid of the container, for example the sample may comprise some or all of the fluid carried by the container. For example, the fluid of the fluid container may be tested to determine the composition of the fluid, the resistance of the fluid, the dielectric constant of the fluid, the viscosity of the fluid, and/or the acidity of fluid. For example the characteristic determiner of FIG. 1b may comprise any one or more of the characteristic determiners described above. For example the characteristic determiner of FIG. 1b may comprise an optical radiation source and an optical detector configured to measure optical transmissivity and/or absorption properties of the fluid. The characteristic determiner of FIG. 1b may be configured to determine viscosity of the fluid, for example based on a measurement of its electrical conductivity or by using another type of measurement such as a viscosity cup.

The processor 2 of the apparatus 1 may compare the first characteristic and the second characteristic to determine whether the fluid expected characteristic of the fluid corresponds to the tested characteristic. For example, a fluid in the fluid container may be modified such that the processing of the fluid would differ from the processing of the unmodified fluid. For example, the fluid in the fluid container may be been replaced or a new fluid may have been inserted into the fluid container. The second characteristic of the fluid container corresponds to the expected characteristic of the original fluid prior to the modification or replacement of the fluid. The comparison of the first characteristic, based on a measurement of the fluid, to the second characteristic will allow the processor 2 to determine whether the fluid has been modified, altered, and/or replaced during use and would therefore alter the processing of the fluid by the processor.

The processing of the fluid may be dependent on the nature of how the fluid has been used. For example, where the fluid is a lubricant which is received by an engine the condition of the lubricant is dependent of the operation of the engine. The operation of an engine may be determined based on a number of parameters of the engine. For example, a lubricant which has been used in an engine which has operated with a lower average revolutions per min (RPM) may require different processing, for example reconditioning of the fluid, compared to a lubricant that has been used in an engine with a higher average revolutions per min (RPM), for example requiring disposal. The second characteristic, based on the identity of the container, may correspond to an operating condition of the engine during the period the lubricant has been used. The processing of the lubricant Is determined by comparing the expected condition of the lubricant based on the second characteristic and the tested condition of the lubricant based on the second characteristic.

In the examples shown in FIG. 1a and FIG. 1b the processor 2 of the apparatus 1 receives the first and second characteristics and compares the difference to a stored value. Based on this comparison the processor 2 determines controls the fluid provider 12 according to the appropriate method of processing of the fluid.

For example, when the fluid in the fluid container has been modified such that the processor 2 determines the comparison of the first characteristic to the second characteristic is greater than a threshold value the processor 2 may prevent the extraction of fluid from the fluid container.

FIG. 3 shows a flow chart for the processing of a fluid container. The fluid container is initially received by the apparatus, 300. Once the fluid container has been received by the apparatus the identifier of the apparatus determines the identity of the fluid container, 305. The second characteristic of the fluid of the fluid container is determined from the data obtainer 6 based on the identity of the fluid container, 310. The first characteristic of the fluid of the fluid container is obtained by the characteristic determiner, 315. The first characteristic and the second characteristic of the fluid of the fluid container are received by the processor, 320. Upon receiving the first characteristic and the second characteristic the processor 2 determines the difference between the first characteristic and the second characteristic and compares the difference to a threshold value, 325. If the difference between the first and second characteristic is greater than the threshold value the apparatus does not extract the fluid from the fluid container, 335. When the difference between the first and second characteristic is less than the threshold the apparatus extracts the fluid from the fluid container, 330.

The identity determiner 8 identifies the fluid container from the identifier 16. The identifier may comprise a visual identification, for example a barcode, a QR code, and/or a serial number. In another example the identifier comprises an electromagnetic identifier, for example a RFID tag, a NFC device, a computer readable medium or any other device emitting an electromagnetic signal. The electromagnetic identifier may comprise a memory storing the identity of the fluid container. In one example, the identifier may obtain data from the data store of the fluid container corresponding to the identity of the fluid container. In another example a user may manually enter an identity of the fluid container.

The data obtainer 6 may determine the second characteristic of the fluid in the fluid container 10. The data obtainer 6 may comprise a memory and the second characteristic may be determined based on a look-up table of characteristics of the fluid and the identity of the fluid container stored in the memory. The data obtainer may comprise a receiver, and may be configured to receive a network message comprising the second characteristic. The network message may be received in response to the data obtainer 6 sending data based on the identity to a remote device such as a remote server.

The first characteristic may be measured in-situ where the fluid remains in the fluid container or an ex-situ measurement where the fluid is measured once it has been removed from the fluid container. The in-situ measurement may be made by a sensor coupled to the apparatus, for example via a transmission of electromagnetic radiation through the fluid, a measurement of the weight of the fluid, and/or volume of the fluid. An in-situ measurement may also be made by a sensor coupled to the container, the sensor may, for example, measure the resistance of the fluid, the capacitance of the fluid, the viscosity of the fluid, and/or the acidity of fluid.

In an example described with reference to FIG. 2b the first characteristic of the fluid is measured using an optical measurement. In this example electromagnetic radiation is transmitted into the fluid reservoir via a first window and received from the fluid reservoir by a detector via a second window. In another example, the fluid container comprises a reflective surface, and the electromagnetic radiation is transmitted into the fluid reservoir from a first window, reflected by the reflective surface and received by the detector via the first window.

The processor 2 controls the fluid provider 12 based on the comparison of the first characteristic to the second characteristic. The first characteristic and the second characteristic may be the same characteristic of the fluid. In another example the first characteristic and the second characteristic may be a different characteristic of the fluid, and the difference between the first characteristic and the second characteristic is compared to a threshold based on a relation of the first characteristic to the second characteristic.

In the examples described above the first characteristic is determined based on testing the fluid of the fluid container and the second characteristic is determined based on the identity of the fluid container. The apparatus may also obtain a first characteristic based on data stored on the data store of the fluid container and obtain a second characteristic from a remote memory based on the identity of the fluid container.

For example, an embodiment of the present disclosure comprises an identity determiner 8 configured to determine an identity of a removable fluid container; a characteristic determiner configured to obtain a first characteristic based on data stored remotely from the fluid container; a data obtainer 6 configured to obtain a second characteristic based on the identity; and a processor 2 configured to control a fluid provider 12 to provide fluid from the removable fluid container based on the comparison of the first characteristic and the second characteristic. In this example, the processor 2 may compare the second characteristic obtained from a remote memory to the first characteristic stored locally on a data store of the fluid container. Based on this comparison the apparatus may determine whether the data stored locally on the memory of the container corresponds to the data stored remotely, and verify one or more characteristics of the fluid of the fluid container. In one example, the remote memory may be a memory coupled to the engine, e.g. a memory of the ECU, and the apparatus may compare the data stored in this memory to data stored locally on the data store of the fluid container. These embodiments may also comprise characteristic determiners which obtain data by testing characteristics of the fluid, and the processor 2 may be configured to control the fluid provider 12 based on the characteristics obtained from memories (remote and local) and the tested characteristics of the fluid.

In these embodiments the apparatus may also comprise a communication interface configured to communicate with a vehicle in which the container has been used to obtain the first characteristic, this may comprise communicating with an engine control unit of the vehicle, for example via a CANBUS protocol. In some embodiments the characteristic determiner is configured to send a network message to a remote device to obtain the first characteristic.

With reference to the drawings in general, it will be appreciated that schematic functional block diagrams are used to indicate functionality of systems and apparatus described herein. It will be appreciated however that the functionality need not be divided in this way, and should not be taken to imply any particular structure of hardware other than that described and claimed below. The function of one or more of the elements shown in the drawings may be further subdivided, and/or distributed throughout apparatus of the disclosure. In some embodiments the function of one or more elements shown in the drawings may be integrated into a single functional unit.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

In some examples, one or more memory elements can store data and/or program instructions used to implement the operations described herein. Embodiments of the disclosure provide tangible, non-transitory storage media comprising program instructions operable to program a processor 2 to perform any one or more of the methods described and/or claimed herein and/or to provide data processing apparatus as described and/or claimed herein.

The activities and apparatus outlined herein may be implemented using controllers and/or processors which may be provided by fixed logic such as assemblies of logic gates or programmable logic such as software and/or computer program instructions executed by a processor. Other kinds of programmable logic include programmable processors, programmable digital logic (e.g., a field programmable gate array (FPGA), an erasable programmable read only memory (EPROM), an electrically erasable programmable read only memory (EEPROM)), an application specific integrated circuit, ASIC, or any other kind of digital logic, software, code, electronic instructions, flash memory, optical disks, CD-ROMs, DVD ROMs, magnetic or optical cards, other types of machine-readable mediums suitable for storing electronic instructions, or any suitable combination thereof.

The invention claimed is:

1. An apparatus comprising:
    an identity determiner configured to determine an identity of a fluid container removed from a vehicle;
    a characteristic determiner configured to obtain a first characteristic based on testing the fluid of the fluid container;
    a data obtainer configured to obtain a second characteristic based on the identity;
    a fluid provider configured to extract fluid from the fluid container; and
    a processor configured to compare the first characteristic and the second characteristic, and to control the fluid provider to extract fluid from the fluid container based on the comparison of the first characteristic and the second characteristic.

2. The apparatus of claim 1, wherein the characteristic determiner is configured to test the fluid in the fluid container so as to determine the first characteristic of the fluid of the fluid container.

3. The apparatus of claim 1, wherein the characteristic determiner is configured to determine the first characteristic via an interface of the fluid container.

4. The apparatus of claim 1, wherein the data obtainer is configured to obtain the second characteristic from a data store based on the identity.

5. The apparatus of claim 1, wherein the identity determiner is configured to read a machine readable marker carried by the container to determine the identity of the removable fluid container.

6. The apparatus of claim 1, wherein the identity determiner is configured to read data of a data store to determine the identity of the removable fluid container.

7. The apparatus of claim 1, wherein the second characteristic comprises an operational history of a vehicle during the time period the fluid container was installed in the vehicle.

8. The apparatus of claim 1, wherein the second characteristic comprises at least one of the amount, temperature, pressure, viscosity, viscosity index, density, electrical resistance, dielectric constant, opacity, chemical composition and origin of the fluid in the fluid container.

9. An apparatus comprising:
an identity determiner configured to determine an identity of a removable fluid container;
a characteristic determiner configured to obtain a first characteristic based on data carried by the removable fluid container;
a data obtainer configured to obtain a second characteristic based on the identity;
a fluid provider configured to extract fluid from the removable fluid container;
and a processor configured to compare the first characteristic and the second characteristic, and to control the fluid provider to extract fluid from the removable fluid container based on the comparison of the first characteristic and the second characteristic.

10. The apparatus of claim 9, wherein the characteristic determiner is configured to determine the first characteristic via an interface of the removable fluid container.

11. The apparatus of claim 9, wherein the identity determiner is configured to read a machine readable marker carried by the container to determine the identity of the removable fluid container.

12. The apparatus of claim 9, wherein the identity determiner is configured to read data of a data store to determine the identity of the removable fluid container.

13. The apparatus of claim 9, wherein the second characteristic comprises an operational history of a vehicle during the time period the removable fluid container was installed in the vehicle.

14. The apparatus of claim 9, wherein the second characteristic comprises at least one of the amount, temperature, pressure, viscosity, viscosity index, density, electrical resistance, dielectric constant, opacity, chemical composition and origin of the fluid in the fluid container.

15. An apparatus comprising:
an identity determiner configured to determine an identity of a fluid container;
a characteristic determiner configured to obtain a first characteristic based on data stored remotely from the fluid container;
a data obtainer configured to obtain a second characteristic based on the identity;
a fluid provider configured to extract fluid from the fluid container;
and a processor configured to compare the first characteristic and the second characteristic, and to control the fluid provider to extract fluid from the removable fluid container based on the comparison of the first characteristic and the second characteristic.

16. The apparatus of claim 15 wherein the characteristic determiner is configured to send a network message to a remote device to obtain the first characteristic.

17. The apparatus of claim 15 wherein the network message comprises the identity.

18. The apparatus of claim 15, wherein the identity determiner is configured to read data of a data store to determine the identity of the removable fluid container.

19. The apparatus of claim 15, wherein the second characteristic comprises an operational history of a vehicle during the time period the removable fluid container was installed in the vehicle.

20. The apparatus of claim 15, wherein the second characteristic comprises at least one of the amount, temperature, pressure, viscosity, viscosity index, density, electrical resistance, dielectric constant, opacity, chemical composition and origin of the fluid in the removable fluid container.

* * * * *